United States Patent [19]

Warriner

[11] Plant 4,459

[45] Sep. 11, 1979

[54] ROSE PLANT

[75] Inventor: William A. Warriner, Tustin, Calif.

[73] Assignee: Jackson & Perkins Company, Medford, Oreg.

[21] Appl. No.: 941,247

[22] Filed: Sep. 11, 1978

[51] Int. Cl.[2] ..... A01H 5/00

[52] U.S. Cl. ..... Plt./11

[58] Field of Search ..... Plt./11

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

A heavily branched, upright rose plant of the hybrid tea class that blooms with very large flowers, China Rose bud color, opening to Neyron Rose, and having very little fragrance.

7 Drawing Figures

BACKGROUND OF THE INVENTION

The present invention relates to a new and distinct variety of rose plant of the hybrid tea class which was originated by me by crossing an unnamed pink hybrid tea rose with pollen from the variety First Prize, U.S. Plant Pat. No. 2,774.

The primary objective of this breeding was to produce a new rose variety of the hybrid tea class, similar to its parent First Prize, but with certain distinctive differences, particularly in the color of the flowers. This objective was substantially achieved, along with other desirable improvements as evidenced by the following unique combination of characteristics which are outstanding in this new variety and which distinguish it from its parents and from all other varieties of which I am aware:

1. A heavily branched plant, quite upright in habit, more upright than the variety First Prize.
2. Long buds of Wilson's China Rose opening to blooms of Wilson's Neyron Rose.
3. Very little fragrance.
4. Very large flowers of 20–25 petals.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:
- *Seed parent.*—Seedling.
- *Pollen parent.*—First Prize.

Classification:
- *Botanical.*—Rose hybrid.
- *Commercial.*—Hybrid tea.

FLOWER

Observations made from specimens grown at Irvine, Calif., in June of 1978.

Blooming habit: Continuous.

Bud:
- *Size.*—1¼ to 1½ inches when petals start to unfurl.
- *Form.*—Long.
- *Color.*—When sepals first divide, near China Rose (024/1); when half blown, upper side of petals near China Rose (024/2); lower side of petals, near China Rose (024/2).
- *Sepals.*—Color: Outer surface Scheele's Green (860/1) mottled in irregular areas with Garnet Brown (00918/3); inner surface, Scheele's Green (860/1) covered moderately with whitish tomentum. Three appendaged sepals, lightly appendaged. Two unappendaged sepals, hairy edged.
- *Receptacle.*—Color: Scheele's Green (860/1), shaded in some areas with Garnet Brown (00918/3). Shape: Funnel. Size: Large. Surface: Smooth.
- *Peduncle.*—Length: Short. Surface: Smooth. Color: Bronzy. Strength: Stiff, erect.
- *Opening.*—Petals curl very little.

Bloom:
- *Size.*—Very large. Average open size 6 inches.
- *Borne.*—Singly and several together.
- *Stems.*—Medium to short.
- *Form.*—When first open, high centered. Permanence: Flattens, with outer petal edges slightly curled.
- *Petalage.*—Number of petals under normal conditions: 20 to 25.
- *Color.*—Center of flower: Upper side of petals: Near Neyron Rose (623/2), shading to Neyron Rose (623/1) near outer edges. Reverse side of petals: Neyron Rose (623/1). Base of petals: Small area at point of attachment Mimosa Yellow (602/1). General tonality from a distance: Neyron Rose (623/1).
- *Variegations.*—None.
- *Discoloration.*—Third day: Outer petals begin to darken to a color near Rose Madder (23/1). Center petals first fade to near white, eventually also darken to Rose Madder (23/1).
- *Fragrance.*—Slight.

Petals:
- *Texture.*—Thick.
- *Shape.*—Round.
- *Form.*—Tips slightly recurved.

*Arrangement.*—Loosely imbricated. Petaloids in center, few.

*Persistence.*—Drop off cleanly.

*Lastingness.*—On the plant, fair. As cut flower, fair.

Reproductive parts:

*Stamens, Anthers.*—Large. Color, light yellow. Arrangement, regular around styles.

*Filaments.*—Color: Rose Madder (23/2).

*Pollen.*—Lemon yellow.

*Styles.*—Color: Very pale green.

*Stigmas.*—Color: Egyptian Buff (407/1).

PLANT

Form: Bush.

Growth: Very vigorous, upright, branching.

Foliage: Number of leaflets on normal mid-stem leaves 5 to 7.

*Size.*—Large.

*Quantity.*—Normal.

*Color.*—New foliage: Garnet Brown (00918/3). Old foliage: Parsley Green (00962/3).

Leaflets:

*Shape.*—Oval pointed.

*Texture.*—Upper side, leathery.

*Edge.*—Serrated.

*Serrations.*—Single, small.

*Petiole.*—Rachis: Color, reddish. Underside, prickles.

*Stipules.*—Long, bearded.

*Disease resistance.*—Normally resistant to mildew under normal growing conditions at Irvine, Calif.

Wood:

*New wood.*—Color: Light green to reddish. Bark: Smooth.

*Old wood.*—Color: Brown. Bark: Smooth.

Prickles:

*Quantity.*—On main stalks from base, ordinary. On laterals from stalk, ordinary.

*Form.*—Long base, hooked downward.

*Color when young.*—Red.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its heavily branched, upright plant, China Rose bud color opening to Neyron Rose, and its slight fragrance.

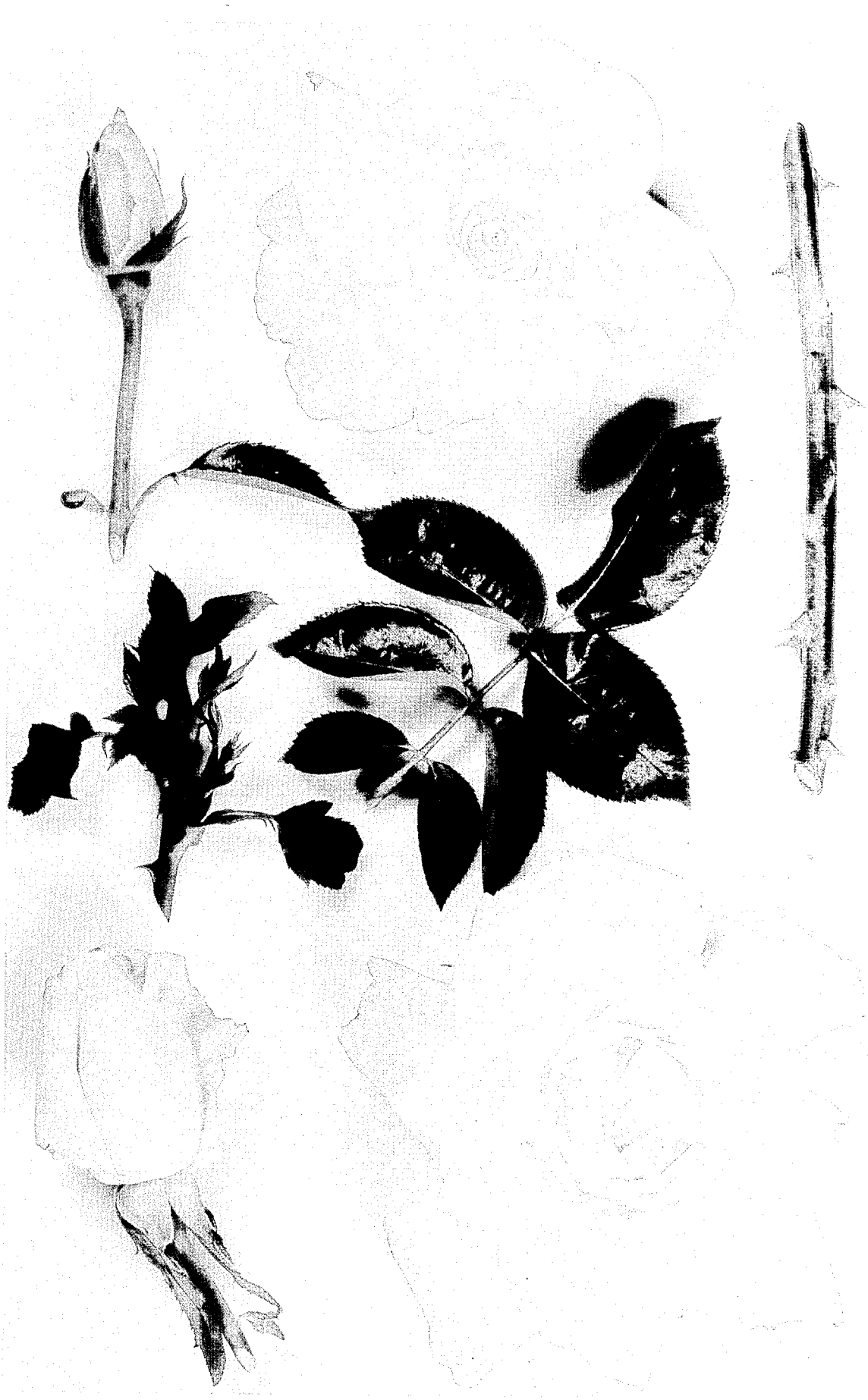

* * * * *